United States Patent
Foote et al.

(10) Patent No.: US 6,715,796 B2
(45) Date of Patent: *Apr. 6, 2004

(54) METHOD FOR SIMULTANEOUSLY PREPARING PHARMACY VIAL LABEL AND DRUG-SPECIFIC WARNING LABELS

(75) Inventors: Richard W. Foote, New Smyrna Beach, FL (US); Carlos R. Young, Bradenton, FL (US)

(73) Assignee: ABP Patent Holdings, LLC, New Smyrna Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/525,268

(22) Filed: Mar. 13, 2000

(65) Prior Publication Data

US 2003/0111837 A1 Jun. 19, 2003

Related U.S. Application Data

(63) Continuation of application No. 09/224,329, filed on Dec. 31, 1998, now Pat. No. 6,036,231, which is a continuation of application No. 08/867,965, filed on Jun. 3, 1997, now Pat. No. 5,855,395, which is a continuation of application No. 08/504,765, filed on Jul. 20, 1995, now Pat. No. 5,642,906, which is a continuation-in-part of application No. 08/121,415, filed on Sep. 16, 1993, now abandoned.

(51) Int. Cl.[7] .............................................. B42D 15/00
(52) U.S. Cl. ............................ 283/67; 40/310; 40/638; 206/570; 281/5; 283/81; 283/101; 428/43
(58) Field of Search ...................... 40/299.01, 310, 40/306, 638; 206/570; 281/2, 5; 283/67, 70, 74, 79, 81, 101, 105, 900, 61, 62; 428/42.1, 43

(56) References Cited

U.S. PATENT DOCUMENTS

| | | | | |
|---|---|---|---|---|
| 4,021,060 A | * | 5/1977 | Seeley et al. | 282/28 R |
| 4,621,729 A | * | 11/1986 | Jackson | 206/37 |
| 4,910,058 A | * | 3/1990 | Jameson | 428/42 |
| 4,976,351 A | * | 12/1990 | Mangini et al. | 206/232 |
| 4,983,438 A | * | 1/1991 | Jameson | 428/42 |
| 5,056,827 A | * | 10/1991 | Sasso | 283/105 |
| 5,129,682 A | * | 7/1992 | Ashby | 283/81 |
| 5,328,208 A | * | 7/1994 | Garrison | 283/105 |
| 5,642,906 A | * | 7/1997 | Foote et al. | 283/67 |
| 5,855,395 A | * | 1/1999 | Foote et al. | 283/67 |
| 6,036,231 A | * | 3/2000 | Foote et al. | 283/67 |

* cited by examiner

Primary Examiner—Monica Carter
(74) Attorney, Agent, or Firm—Allen, Dyer, Doppelt, Milbrath & Gilchrist, P.A.

(57) ABSTRACT

A method for preparing both main label and warning label portions for a container useful in dispensing drugs by a pharmacist in which the main label portion contains specific drug or patient information and the warning label portion contains one or more warnings specific to the drug or patient information includes the steps of providing a backing sheet having the main label portion and the warning label portion releasably adhered thereto, printing the drug or patient information on the main label portion and the drug-specific information on the warning label during only one printing pass, and then affixing both the main label portion and the warning label portion to a drug container.

11 Claims, 4 Drawing Sheets

FIG. 4

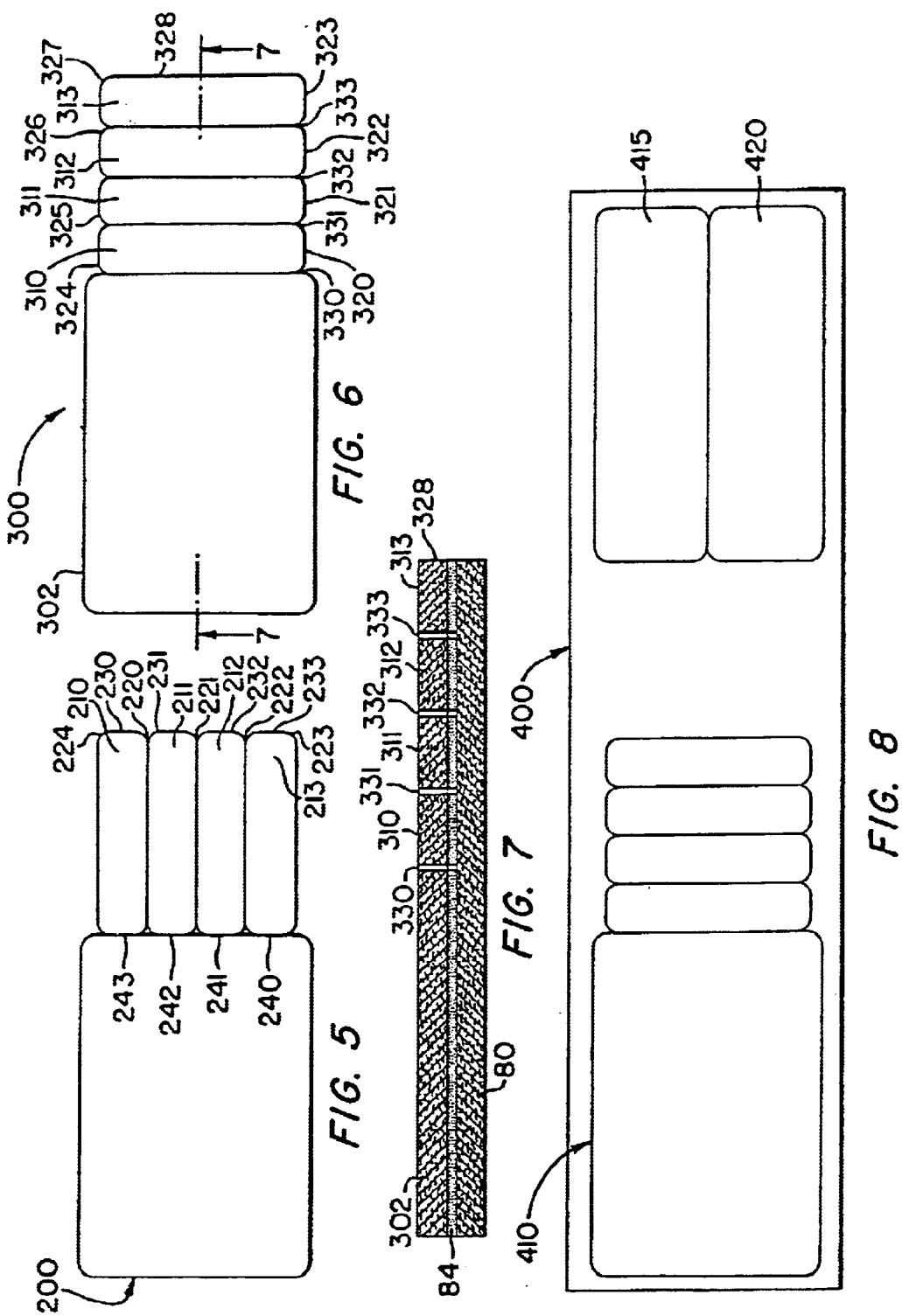

ically printed out receipts for the customer and records for the pharmacy.
METHOD FOR SIMULTANEOUSLY PREPARING PHARMACY VIAL LABEL AND DRUG-SPECIFIC WARNING LABELS This application is a continuation of appln. Ser. No. 09/224,329 filed Dec. 31, 1998, now U.S. Pat. No. 6,036,231 which is a continuation of appln. Ser. No. 08/867,965 filed Jun. 3, 1997, now U.S. Pat. No. 5,855,395, which is a continuation of appln. Ser. No. 08/504,765 filed Jul. 20, 1995, now U.S. Pat. No. 5,642,906, which is a continuation-in-part of appln. Ser. No. 08/121,415 filed Sep. 16, 1993, abandoned.

FIELD OF THE INVENTION

This invention relates to paper blanks for use with a printer in a computer system, and in particular relates to a compound paper blank to be printed on by a computer printer.

BACKGROUND OF THE INVENTION

Labels having pressure sensitive adhesive have been applied to drug containers for a long time by the pharmaceutical industry to identify the customer, the doctor, the drug being dispensed, and the frequency of the dosage. These labels usually can be purchased in bundles that can be fed into a computer driven printer. The information to be printed on one of the labels is either typed into the computer using a conventional pharmacy computer program or is retrieved from a stored record having been previously typed into the computer memory using the pharmacy computer program. Such a computer program also has automatically printed out receipts for the customer and records for the pharmacy.

The pharmaceutical industry has also been applying oblong or rectangular warning labels to the drug containers for some time. These warning labels warn the customer about certain events or provide instructions involving the prescribed drug. For example, a warning label may carry the message:

MAY CAUSE DROWSINESS; ALCOHOL MAY INTENSIFY THIS EFFECT. USE CARE WHEN OPERATING A CAR OR DANGEROUS MACHINERY.

The warning labels have been supplied to the pharmaceutical industry for some time in rolls of the same message.

Pharmacies have also been supplying customers with an instruction sheet containing information about the drugs they are purchasing. One type of such labels carry the brand name PAL (Patient Advisory Leaflet).

The prior art also contains references which teach the use of a computer system to generate prescription labels printed by a computer driven printer. Such references include the following U.S. patents, which are incorporated herein by reference: Baum U.S. Pat. No. 4,918,604; Olodort et al. U.S. Pat. No. 4,875,174; and McKee U.S. Pat. No. 4,972,657. The prior art also contains references which disclose a manual form having an adhesive label portion used in combination for record keeping and generating a label to be applied to a drug container. Examples of U.S. patents, which are incorporated herein by reference, disclosing such forms are the Lockhart patents U.S. Pat. Nos. 4,277,089 and 4,159,129; and the Biava et al. U.S. Pat. No. 4,799,712.

However, there is no known prior art reference which provides a blank for a computer printer that contains portions for both a removable prescription drug label and a removable warning label with portions for other printed information. Such a system would reduce package costs, provide greater flexibility, and be compatible with existing computer software used by pharmacies.

SUMMARY OF THE INVENTION

Accordingly the present invention is designed to provide a multi-part blank which can be fed in a computer driven printer and when printed, will contain all of the parts needed for a complete set. Such a set contains a peelable vial label having a pressure sensitive adhesive connected to removable strips of computer selected warning labels also having a pressure sensitive adhesive. The set also contains portions for printed information needed by both the pharmacy and the customer.

The present invention provides a printer blank which can cut expenses, reduce errors, and cut time in preparing records and drug containers for customers. In one particular embodiment of the invention, a single sheet of multisectional paper blank can be fed into a laser printer and on that one sheet there will be printed a drug advisory leaflet; no, one or more than one warning labels having a pressure sensitive adhesive on its back side for easy application to a drug container, and a drug container label containing drug, customer, and pharmacy information. This blank in one pass through the laser printer contains all of the necessary records and parts for the entire drug transaction.

According to one embodiment, the present invention comprises a blank for use with a printer for printing information and labels for drug containers. The blank comprises a sheet of a material having a front side that can be printed on with the printer, a back side, a top and bottom edge which together define a generally horizontal direction, and two side edges which together define a generally vertical direction. The sheet includes at least a first portion and a second portion divided by a first, generally vertically extending tear line or tear line that extends from the top edge to the bottom edge. In the first portion the printer prints text about the particular drug being prescribed, and in the second portion, which includes a label laminate divided into a first section and a second section by a generally horizontal, second tear line. The second section is further divided into a plurality of horizontal strips by at least two generally horizontal tear lines which extend from the first tear line to one of the side edges of the blank. The laminate is comprised of a backing sheet, a removable label sheet having a front side that can be printed on with the printer and a back side, and a pressure-type adhesive on the back side of said label sheet.

Other advantages, features, and details of the present invention will be set forth in or apparent from the detailed description thereof contained hereinbelow.

BRIEF DESCRIPTION OF THE DRAWINGS

FIG. 2 is a plan view of a blank in accordance with the present invention before it has been printed on;

FIG. 4 is a plan view of a blank that has indicia printed on it by a computer driven laser printer;

FIGS. 5, 6 and 8 are plan views of other blanks in accordance with the present invention; and FIG. 7 is an enlarged, not-to-scale, cross-sectional view taken along lines 7—7 of FIG. 6 in which certain layers have been shown thicker in order to depict the details of construction.

DESCRIPTION OF THE PREFERRED EMBODIMENT

Figure 1:
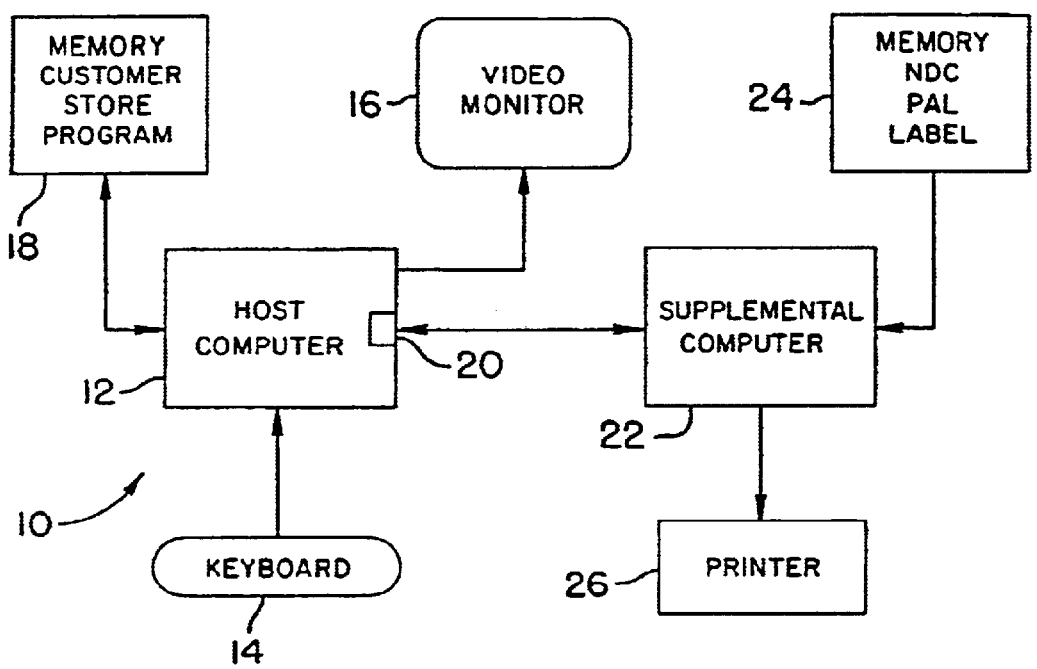
FIG. 1 is an electronic block diagram of a prototype computer system used to demonstrate the present invention.
Figure 4:
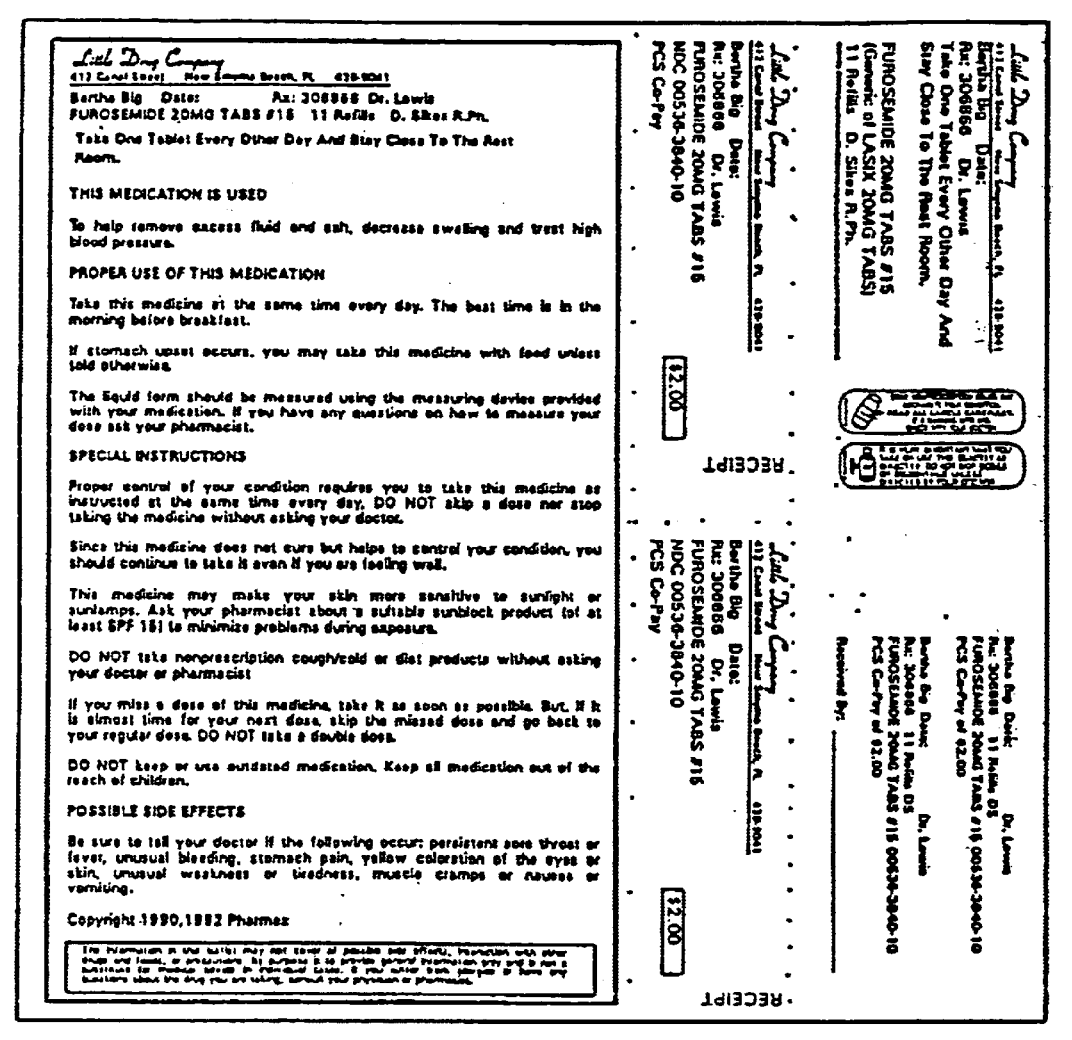

With reference now to the drawings in which like numerals are used to represent like elements throughout the several views, and in particular with reference to FIG. 1, a computer system 10 is depicted for generating a completed form such as shown in FIG. 4. Computer system 10 is comprised of a conventional host computer 12 having a conventional keyboard 14 for the manual input of information, a conventional computer monitor 16 for the output of information and a conventional external memory 18, which can be a conventional hard disk system. Host computer 12 has an input/output port 20 and can be an IBM compatible computer type using an INTEL brand 80486 DX microprocessor with 8 Mega-bytes of internal memory. Memory 18 holds a number of data bases, such as a customer data base containing customer information and a store data base containing the pharmacy's inventory control information. Memory 18 also holds a conventional pharmaceutical computer program. The program is used by pharmacies to generate the customer data base and store data base, and to extract information contained in these data bases and combine it with information entered from keyboard 14 by a pharmacist to produce an output to drive a printer to print a conventional drug label.

Connected to host computer through input/output port 20 is a supplemental computer 22. Supplemental computer 22 can be identical in configuration to host computer 12. Connected to supplemental computer 22 is a conventional external memory 24 and a conventional laser printer 26, such as a Hewlett-Packard model Series 2 laser printer. Stored in memory 24 are an NDC (National Drug Code) data base containing a standardized drug code list, a data base containing information for the customer about each prescribed drug, such as the commercially available C-PAL® data base, and a data base of warning labels, including unique logos and icons (see, for example, FIG. 4). Also contained in memory 24 is a program which permits supplemental computer to intercept the printer information from host computer 12, to reformat the information, to enter the C-PAL® and warning label data bases to get the related information, and to regenerate the printer information with the incorporated C-PAL® and warning label information.

Computer system 10 is depicted in FIG. 1 as having two computers and it is so configured because it has been designed to complement, upgrade and modify an existing pharmacy computer system that has been using commercially available software. However, an alternative embodiment of the invention (not depicted) is implemented on, or includes, a single computer system in which supplemental computer 22 is combined with host computer 12, supplemental computer memory 24 is combined with host computer memory 18, and a single computer program is used both for the conventional pharmacy inventory control, accounting and report generating tasks and for the printing of a completed form, such as depicted in FIG. 4.

Figure 2:
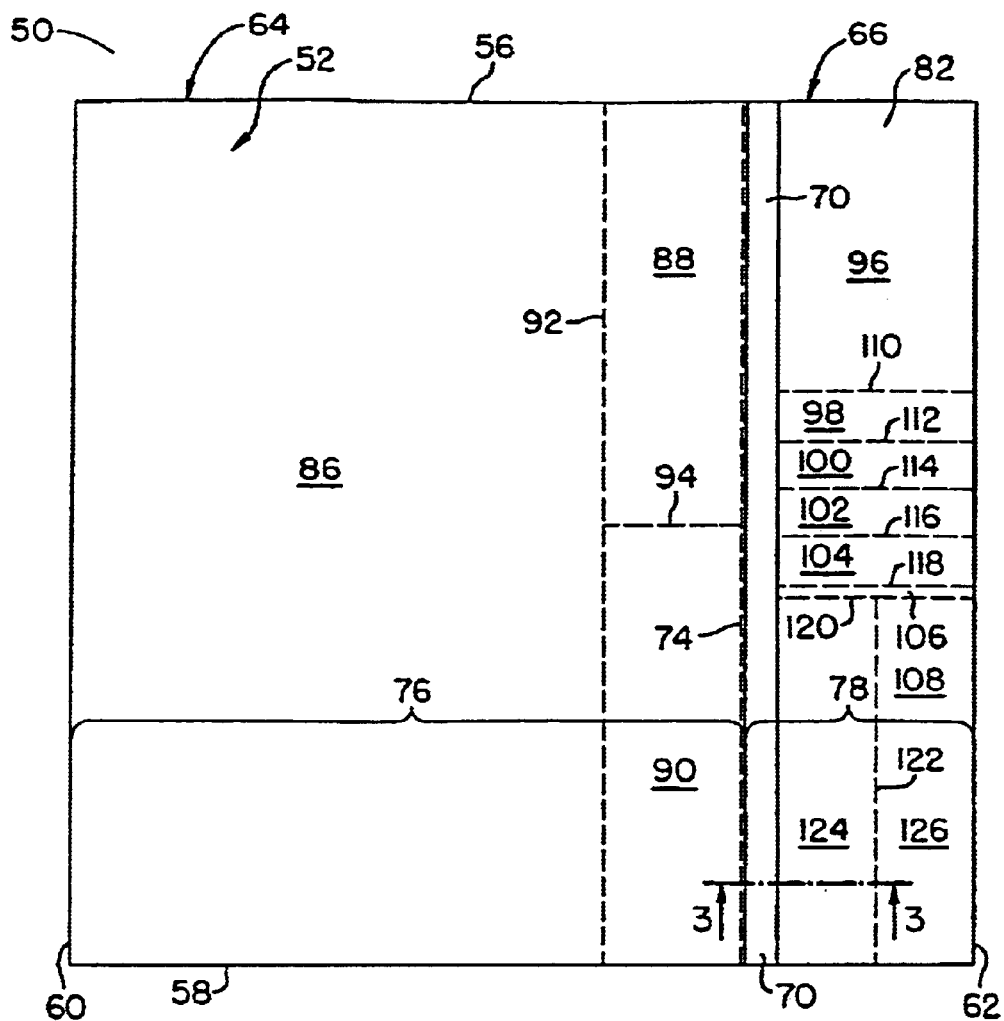
Figure 3:
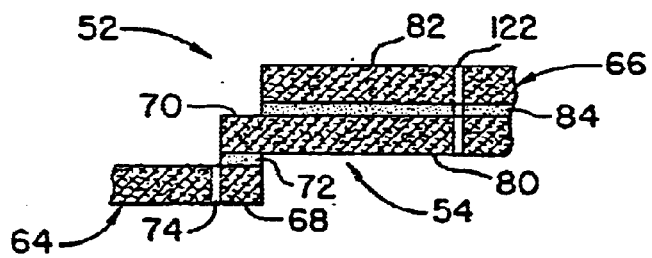
FIG. 3 is an enlarged, not-to-scale, cross-sectional view taken along lines 3—3 of FIG. 2 in which certain layers have been shown thicker in order to depict the details of construction.

A blank or form 50 in accordance with the present invention is depicted in FIGS. 2 and 3. Blank 50 is preferably made from a flexible, conventional stock material. Blank 50 has a front side 52 which can receive and retain "ink" or print from printer 26 and a back side 54 (FIG. 3). As shown in FIG. 2, blank 50 has a top edge 56 and a bottom edge 58 parallel thereto which are arbitrarily used to define the-horizontal direction in blank 50. Blank 50 also has a left side 60 and a right side 62 parallel thereto which are arbitrarily used to define the vertical direction in blank 50. In a presently preferred embodiment, blank 50 is made of paper and is essentially a square with each side having a length of 8.5 inches (21.59 cm). Alternatively, blank 50 can be made from a plastic or other thin sheet material which can be printed on.

Blank 50 is comprised of a first sheet 64 and a second sheet 66 which have respective overlapping strips 68 and 70 that are adhered to one another with a conventional heat set adhesive 72, as shown in FIG. 3.

Strip 68 is defined not only by its overlapping strip 70, but also by a vertically extending tear line 74 that extends from top edge 56 to bottom edge 58. Tear line 74 can be a score line, but preferably is a perforation line with the perforations extending completely through first sheet 64. Thus, as seen on front side 52 of blank 50, it can also be said that tear line 74 divides blank 50 into a first portion 76, which is coextensive with first sheet 64 less strip 68, and a second portion 78 which is coextensive with second sheet 66 including strip 70.

As depicted in FIG. 3, second sheet 66 is comprised of a laminate and has a backing 80 and a paper top layer 82. Backing 80 in the presently preferred embodiment is a paper product having an embedded plastic top portion or coated with a plastic film (not shown). Attached to the underside of top layer 82 is a conventional pressure adhesive 84. By appropriately selecting top layer 82, adhesive 84 and backing 80, adhesive 84 removably adheres top layer 82 to backing 80, and after top layer 82 is removed from said backing sheet is able to adhere more permanently top layer 82 to a container (not shown), which can be a conventional plastic bottle in which drugs are dispensed.

As seen in FIG. 2, when viewed together with FIG. 4, first portion 76 is much larger in the horizontal direction than second portion 78. In a presently preferred embodiment, first sheet has a width of 6⅝th inches (16.83 cm) and first portion 76 has a width of 6⅜ inches (16.19 cm). First portion 76 is divided into three sections, 86, 88 and 90 by a vertical tear line 92 and by a short horizontal tear line 94. Tear line 92 is a perpendicular bisector of tear line 92, which is parallel to tear line 74 and similarly extends from top edge 56 to bottom edge 58. In a preferred embodiment of the invention, tear lines 92 and 94 are perforation lines with the perforation extending completely through first sheet 64. As shown in FIG. 4, section 86 is the largest section and is used to contain the text of a Patient Advisory Leaflet. Sections 88 and 90 are obviously of equal size and they are each used to contain the text of a customer receipt which can be used for financial records.

Second portion 78 is divided into a plurality of vertically arranged portions by a plurality of horizontal tear lines. In the present embodiment there are seven such portions denoted 96, 98, 100, 102, 104, 106 and 108 created by six tear lines 110, 112, 114, 116, 118, and 120. In a preferred embodiment, tear lines 110, 112, 114, 116 and 120 extend only through top layer 82 and attached layer of adhesive 84 and are perforation lines. On the other hand, tear line 118 in a preferred embodiment is a perforation line with the perforations extending completely through second sheet 66. Portion 96 is a wrap-around label to be applied to a drug container. Portions 98, 100, 102 and 104 are four blanks, none, some or all of which may be used to contain design and word indicia representing warning labels to be applied to a drug container. Portion 106 is unused filler.

Portion 108 is vertically bisected by a vertical tear line 122 to create vertically extending parts 124 and 126. In a preferred embodiment, tear line 122 is a perforation line with the perforations extending completely through second sheet 66. Part 124 is used to obtain a third party signature and also to contain information about the particular prescription. Part 126 can be used as an adhesive pharmacy record label to be applied to an appropriate ledger page (not shown).

The advantages to having tear lines 74, 92, 94, 118 and 122 extend completely through their respective sheets 64 and 66 is that blank 50 can be easily and quickly divided into five portions, each with an entirely different purpose. Portions 86 (the patient advisory leaflet), 88 and 90 are adhesive free and are given to the customer. Combined portions 96, 98, 100, 102 104 contain indicia having the information necessary for the container of the drug being dispensed, and the adhesive top layer 82 can be removed as one piece from backing 80, the unused warning label portions removed, and the remaining piece applied to the drug container. Finally, adhesive parts 124 and 126 can be selectively removed from their piece of backing 80 and applied to the appropriate pharmacy ledger.

The number of warning label blanks provided is somewhat arbitrary, except that based upon prior experience most druggist do not select more than four such labels for any particular drug. obviously, the number of blanks could be larger or smaller if necessary, and the unused blanks would be separated and discarded before the drug label, portion 98, and used warning labels, portions 98, 100, 102 and 104 are applied.

In an alternative embodiment, portion 108 could be divided into three vertically extending parts by two tear lines so that the signature section could be separated from the pharmacy record label.

The further embodiments depicted in FIGS. 5–8 may be used alone as illustrated or as alternative portions of the particular embodiment described above.

The FIG. 5 embodiment comprises a main label 200 and auxiliary labels 210 to 213. Auxiliary labels 210 to 213, which are horizontally disposed with respect to main label 200, are horizontally separated from each other and from other portions of the blank by way of knife or die cuts 220 to 224 and vertically from other portions of the blank by way of knife or die cuts 230 to 233, which knife or die cuts extend through the adhesive layer but not through the backing layer. At least one of lines 240 to 243 is a perforation line extending to but not through the backing sheet, such that at least one of auxiliary labels 210 to 213 is separated from the backing sheet simultaneously with the removal of main label 200 from the backing sheet. Any of lines 240 to 243 which are not perforation lines, if any, are knife or die cuts extending to the backing sheet, such that the respective auxiliary labels are completely separated from each other as well as from any other portions of the blank.

The embodiment of FIGS. 6 and 7 differs from the FIG. 5 embodiment in that auxiliary labels 310 to 313 are vertically rather than horizontally disposed with respect to the main label 300. Thus each of lines 320 to 328 is a knife or die cut extending through adhesive 84 to but not through backing sheet 80, at least line 330 of lines 330 to 333 is a perforation line extending to but not through back sheet 80, and any of lines 331 to 333 which are not perforation lines, if any, are knife or die cuts extending to but not through the backing sheet, such that any respective auxiliary label is completely separated, and therefore separately removable, from any other portion of the blank. With such a construction, at least one but optionally up to all of the auxiliary labels may be removed from the backing sheet simultaneously with the main label and any unused but removed auxiliary labels, if any, may be subsequently and easily separated from the main and/or used auxiliary label (s). In a preferred embodiment of the FIGS. 6 and 7 embodiment, lines 330 and 331 are perforated lines and lines 332 and 333 are die cuts, such that two auxiliary labels 310 and 311 are simultaneously removed from back sheet 80 with main label 302.

The embodiment of FIG. 8 illustrates a blank 400 of which the blank of the FIG. 6 embodiment is one component 410. Additional components 415 and 420 of the FIG. 8 embodiment are additional separately removable adhesive labels.

As described in detail above, in carrying out a method of labeling utilizing blank forms according to the invention, the user causes the desired information to be printed on the main label and, optionally, on one or more auxiliary labels, simultaneously removes the printed main label and at least one auxiliary label from the backing sheet, separates any simultaneously removed but unused auxiliary label(s), and simultaneously applies the main label and any remaining, i.e., used, auxiliary label(s) to another surface. When used in a pharmacy application as a labeling system for prescription drugs, any used auxiliary labels comprise warning labels to the user of the drug dispensed in the container to which the labels are affixed.

Thus, the present invention has been described with reference to the drawings with respect to presently preferred embodiments. As such, the present invention permits, for example, the existing computer system of a pharmacy to execute a label set as usual while the software of the present invention adds information by which laser printer 26 will print any warning labels and an advisory leaflet corresponding to the drug being dispensed. The one piece wrap-around pressure sensitive label for the drug container optionally combines the main drug container label with one or more selected warning labels.

Other modifications and enhancements of the present invention would be obvious to those skilled in the art.

We claim:

1. A method for preparing both main label and warning label portions for a container useful in dispensing drugs by a pharmacist, in which the main label portion contains specific drug or patient information and the warning label portion contains one or more warnings specific to the drug or patient information contained on the main label portion, the method comprising the steps of:

providing a backing sheet having the main label portion and the warning label portion releasably adhered thereto, both the main label portion and the warning label portion having respective outer surfaces for receiving printed information thereon;

printing the drug or patient information on the main label portion and the drug-specific information on the warning label during only one printing pass;

removing both the main label portion and the warning label portion from the backing sheet; and thereafter affixing both the main label portion and the warning label portion to a drug container.

2. The method recited in claim 1 further comprising the step of removably attaching the warning label portion along a side of the main label portion such that the removal of the main label portion permits the simultaneous removal of at least a part of the warning label portion.

3. The method recited in claim 1 further comprising the step of printing text on the warning label portion in a direction generally lateral to the direction of printing along the main label portion.

4. The method recited in claim 1 further comprising the step of forming the main label portion and the warning label portion as an elongated composite label.

5. The method recited in claim 1 wherein the warning label portion comprises two or more individual warning labels, further comprising the steps of partially perforating the warning label portion to form a tear line between adjacent warning labels, whereby two or more adjacent individual warning labels may be removed together from the backing sheet and either (a) affixed together onto the drug container or (b) removed together from the backing sheet and then separated, or (c) separated from each other as one or more individual labels are removed from the backing sheet.

6. The method recited in claim 5 further comprising the steps of extending a sheet of printable paper from the main label and warning label portions, and printing a patient advisory leaflet onto an outer surface of the paper sheet during the one printing pass.

7. The method recited in claim 6 further comprising the step of providing an auxiliary label portion releasably adhered to the backing sheet, and printing auxiliary information thereon during the one printing pass.

8. A method for the realtime preparation of a pharmacy label set having a main vial label containing customer-specific drug and dosage information printed thereon and one or more warning labels each containing a drug-specific warning thereon, the method comprising the steps of:

providing a printer;

connecting computer means and database means with the printer so as to supply an electronic data input to the printer containing the customer-specific drug and dosage information and the drug-specific warning information;

providing a plurality of blank forms each of which has an upper surface and a lower surface with an adhesive backing on the lower surface, the upper surface of each form defining adjacent printable blank vial label and warning label sections for receiving printing of the customer-specific drug and dosage information and the warning label information, respectively, on the upper surface thereof;

passing each form through the printer and, in one pass, printing—
  (a) the customer-specific drug and dosage information on the vial label section of the form; and
  (b) drug-specific warning information on at least one warning label of the section of the form; and attaching the vial label section and at least a portion of the warning label section to a drug container.

9. The method recited in claim 8, further comprising the step of processing each form so that the vial label section and the warning label section are removable together from a backing sheet.

10. The method recited in claim 9, further comprising the step of processing each form so that the vial label section is removable together with an adjacent warning label.

11. The method recited in claim 9, further comprising the step of processing each form so that at least one warning label is removable with the vial label section and readily separated therefrom.

* * * * *